United States Patent [19]

Hess et al.

[11] 4,243,595
[45] Jan. 6, 1981

[54] 15-SUBSTITUTED-OMEGA-PENTANOR-PROSTAGLANDINS

[75] Inventors: Hans-Jurgen E. Hess, Old Lyme; Michael R. Johnson, Gales Ferry; Jasjit S. Bindra, Groton; Thomas K. Schaaf, Old Lyme, all of Conn.

[73] Assignee: Pfizer Inc., New York, N.Y.

[21] Appl. No.: 705,769

[22] Filed: Jul. 15, 1976

Related U.S. Application Data

[60] Division of Ser. No. 485,491, Jul. 3, 1974, Pat. No. 3,974,213, which is a continuation-in-part of Ser. No. 425,519, Dec. 17, 1973, abandoned, which is a continuation-in-part of Ser. No. 271,220, Jul. 13, 1972, abandoned.

[30] Foreign Application Priority Data

Jul. 4, 1973 [NZ] New Zealand ..................... 171269

[51] Int. Cl.$^3$ ................ C07D 309/12; C07D 317/44
[52] U.S. Cl. ..................... 260/345.7 P; 260/340.5 P
[58] Field of Search .................. 260/345.7 P, 340.5 P

[56] References Cited

U.S. PATENT DOCUMENTS

| 3,678,092 | 7/1972 | Finch | 260/345.8 |
|---|---|---|---|
| 3,821,279 | 6/1974 | Kurono et al. | 260/340.5 P |
| 3,887,587 | 6/1975 | Schaaf et al. | 260/345.7 |
| 3,931,289 | 1/1976 | Bundy | 260/345.7 |
| 3,962,312 | 6/1976 | Hayashi et al. | 260/345.7 |
| 3,984,424 | 10/1976 | Schaaf et al. | 260/340.5 P |

*Primary Examiner*—Nicky Chan
*Attorney, Agent, or Firm*—Connolly and Hutz

[57] ABSTRACT

The 15 aryl substituted-ω-pentanorprostaglandins and various intermediates employed in their preparation. The novel prostaglandins of this invention have been found to have activity profiles comparable to the parent prostaglandins, but exhibit a greater tissue specificity of action.

4 Claims, No Drawings

15-SUBSTITUTED-OMEGA-PENTANORPROSTA-GLANDINS

CROSS REFERENCE TO RELATED APPLICATIONS

This application is a division of application Ser. No. 485,491, filed July 3, 1974 and now U.S. Pat. No. 3,974,213, which, in turn, is a continuation-in-part of application Ser. No. 425,519 filed Dec. 17, 1973, and now abandoned, which, in turn, is a continuation-in-part of application Ser. No. 271,220 filed July 13, 1972 and now abandoned.

BACKGROUND OF THE INVENTION

This invention relates to certain novel analogs of the naturally occurring prostaglandins. In particular, it relates to novel 15-substituted-ω-pentanorprostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom, et al., *Acta Physiol. Scand.* 64:332-33 1965 and Bergstrom, et al., *Life Sci.* 6:449-455, 1967) and lower systemic arterial blood pressure (vasodepression) on intravenous administration (Weeks and King, *Federation Proc.* 23:327, 1964; Bergstrom, et al., 1965, op. cit.; Carlson, et al., *Acta Med. Scand.* 183:423-430, 1968; and Carlson, et al., *Acta Physiol. Scand.* 75:161-169, 1969). Another well known physiological action for $PGE_1$ and $PGE_2$ is as a bronchodilator (Cuthbert, *Brit. Med. J.* 4:723-726, 1969).

Still another important physiological role for the natural prostaglandins is in connection with the reproductive cycle. $PGE_2$ is known to possess the ability to induce labor (Karim, et al., *J. Obstet. Gynaec. Brit. Cwlth.* 77:200-210, 1970), to induce therapeutic abortion (Bygdeman, et al., *Contraception*, 4, 293 (1971) and to be useful for control of fertility (Karim, *Contraception*, 3, 173 (1971)). Patents have been obtained for several prostaglandins of the E and F series as inducers of labor in mammals (Belgian Patent No. 754,158 and Wester German Pat. No. 2,034,641), and on $PGF_1$, $F_2$, and $F_3$ for control of the reproductive cycle (South African Patent 69/6089). It has been shown that luteolysis can take place as a result of administration of $PGF_2\alpha$ [Labhsetwar, Nature 230 528 (1971)] and hence prostaglandins have utility for fertility control by a process in which smooth muscle stimulation is not necessary.

Still other known physiological activities for $PGE_1$ are in the inhibition of gastric acid secretion (Shaw and Ramwell, In: *Worcester Symp. on Prostaglandins*, New York, Wiley, 1968, p. 55-64) and also of platelet aggregation (Emmons, et al., *Brit. Med. J.* 2:468-472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.*, 81, 396 (1971) and references cited therein). It has been shown that placing a 15-alkyl group in the prostaglandins has the effect of increasing the duration of action possibly by preventing the oxidation of the C15-hydroxyl [Yankee and Bundy, JACS 94, 3651 (1972)], Kirton and Forbes, *Prostaglandins*, 1, 319 (1972).

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (*Lancet*, 536, 1971).

SUMMARY OF THE INVENTION

These needs are met by the novel compounds of this invention, the 13,14 dihydro 15 aryl substituted-ω-pentanorprostaglandins in which the aryl substituent in question is α- or β-naphthyl; phenyl; 3,4-methylenedioxyphenyl; 3,4-dimethoxyphenyl; 3,4,5-trimethoxyphenyl; or monosubstituted phenyl wherein said substituent is halo, trifluoromethyl, phenyl, lower alkyl or lower alkoxyl.

The preferred novel prostaglandin analogs of the present invention are those of the formula:

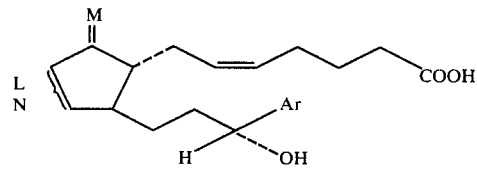

wherein
Ar is α- or β-naphthyl; phenyl; 3,4-dimethoxyphenyl; 3,4-methylenedioxyphenyl; 3,4,5-trimethoxyphenyl; or monosubstituted phenyl wherein said substituent is halo, trifluoromethyl, phenyl, lower alkyl or lower alkoxy;
L is a single bond or cis double bond;
M is =O or

N is hydrogen or α-hydroxyl;
and wherein L, M and N are so selected as to complete the structure of a prostaglandin of the A, F or E series.

Another preferred group of compounds of the present invention are those of the formula

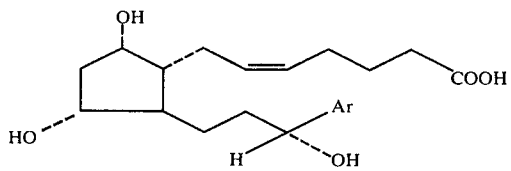

Still another preferred group of novel prostaglandin analogs of the present invention are those of the formula:

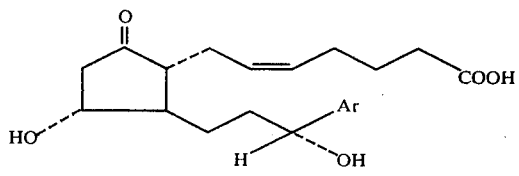

Yet another preferred group of compounds of the present invention comprises those of the formula

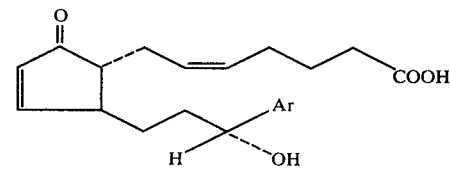

wherein Ar is as defined above.

In addition to the 15-substituted-ω-pentanorprostaglandins wherein the prostaglandin is 13,14-dihydro $PGA_2$, 13,14-dihydro $PGF_{2\alpha}$ and 13,14-dihydro $PGE_2$, this invention further comprises a compound of the structure:

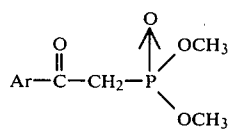

wherein Ar is α- or β-naphthyl; 3,4-methylenedioxyphenyl; 3,4-dimethoxyphenyl; 3,4,5-trimethoxyphenyl or monosubstituted phenyl wherein said substituent is halo, trifluoromethyl, phenyl, lower alkyl or lower alkoxyl; a useful reagent for preparation of the novel prostaglandins; and useful intermediates for these prostaglandins as follows:

a compound of the structure:

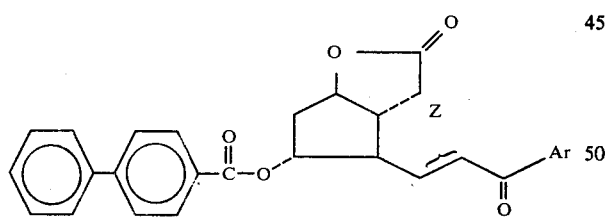

a compound of the structure: wherein Z is a single bond or trans double bond;

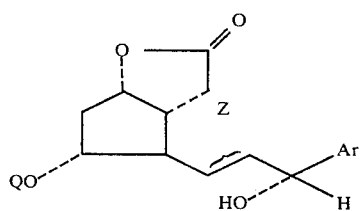

wherein Q is hydrogen or parabiphenylcarbonyl;
a compound of the structure:

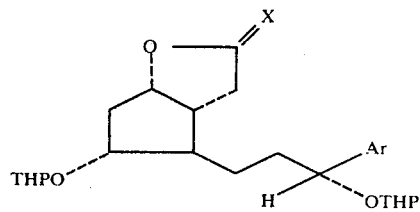

wherein THP is tetrahydropyranyl, and X is O or

a compound of the structure:

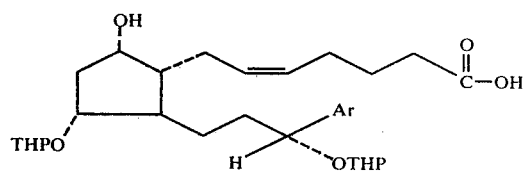

a compound of the structure:

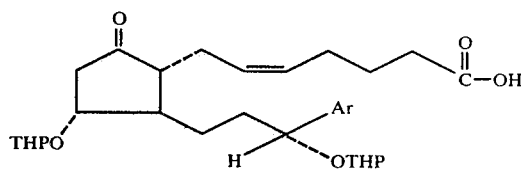

wherein THP and Ar are as previously defined,
and especially 13,14-dihydro-15-phenyl-ω-pentanor $PGE_2$.

It will be understood by those skilled in the art that in structures depicting hemiacetals, no sterochemistry is implied at the lactol carbon.

It will be further understood that as herein used, the expression "prostaglandin of the 'zero' series," for example $PGE_0$, refers to prostaglandins in which the 5-6 and 13-14 double bonds have been saturated; i.e.: $PGE_0$ is 5,6, 13,15 tetrahydro $PGE_2$. In addition, the phrases "zero series," "one series" or "two series" as herein employed refer to the degree of unsaturation in the side chains, e.g. $PGE_2$, $PGA_2$, are prostaglandins of the "two series" whereas $PGE_1$ and $PGA_1$ are prostaglandins of the "one series". Furthermore as herein employed the phrase "lower alkyl group" refers to alkyl groups containing from 1 to 4 carbon atoms.

Scheme A

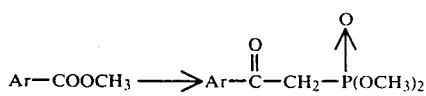

-continued
Scheme A

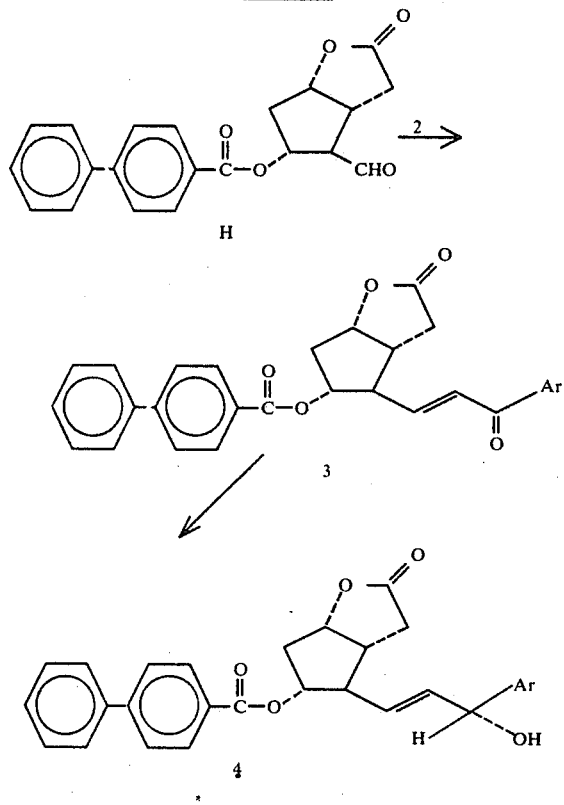

-continued
Scheme A

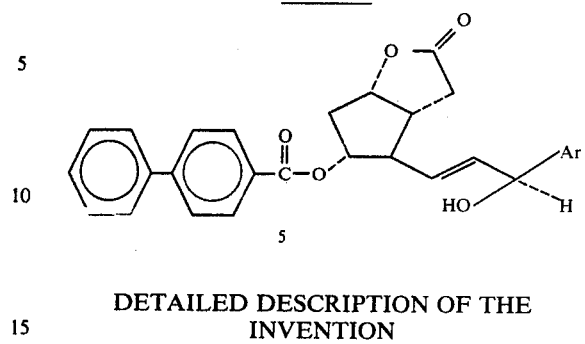

DETAILED DESCRIPTION OF THE INVENTION

As shown in Scheme A, the first step (1→2) is the condensation of the appropriate ester with a dialkyl methylphosphonate to produce ketophosphonate 2. Typically, the desired methyl ester is condensed with dimethyl methyl phosphonate.

In 2→3 the ketophosphonate 2 is caused to react with the known [Corey et al., *J. Org. Chem.* 37, 3043 (1972)] aldehyde H to produce, after chromatography or crystallization, the enone 3. The enone 3 can be reduced with zinc borohydride to a mixture of alcohols, 4 and 5 which may be separated by column or high pressure liquid chromatography. In this reaction ethers such as tetrahydrofuran or 1,2 dimethoxy ethane are usually employed as solvents. Further transformations of 4 are shown on Scheme B.:

4→6 is a base catalyzed transesterification in which the p-biphenyl-carbonyl protecting group is removed. This is most conveniently conducted with potassium carbonate in methanol or methanol-tetrahydrofuran solvent. 6→7 involves the protection of the two free hydroxyl groups with an acid-labile protecting group. Any sufficiently acid labile group is satisfactory; however, the most usual one is tetrahydropyranyl, which can be incorporated in the molecule by treatment with dihydropyran and an acid catalyst in an anhydrous medium. The catalyst is usually p-toluenesulfonic acid.

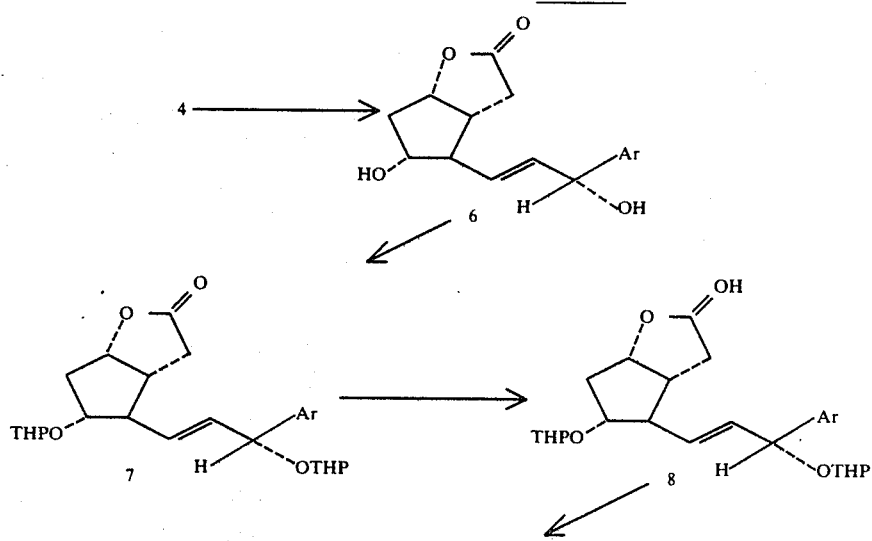

Scheme B

-continued
Scheme B

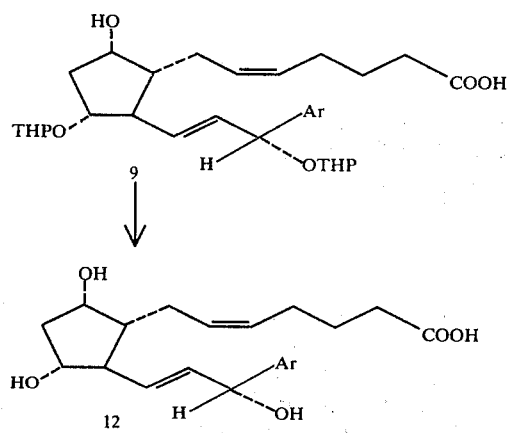
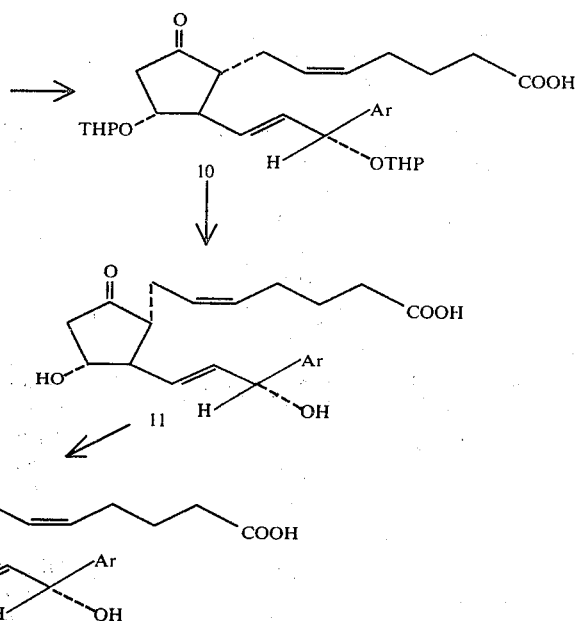

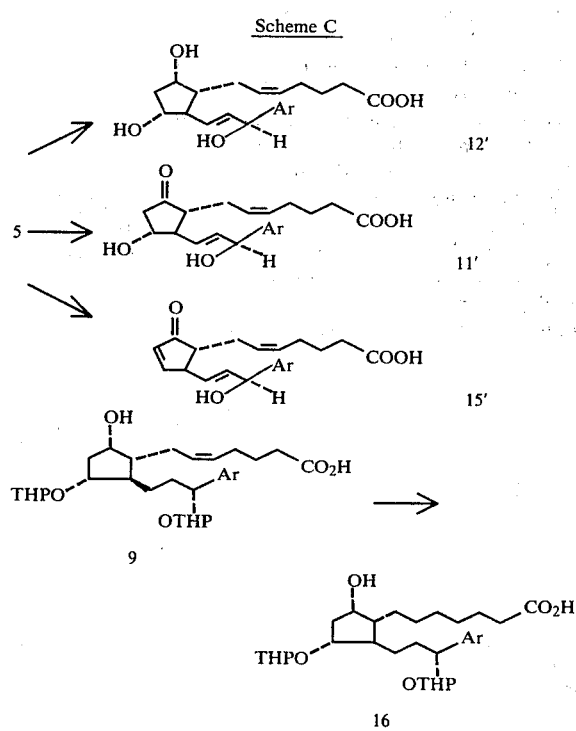

Scheme C

7→8 is a reduction of the lactone 7 to the hemiacetal 8 using diisobutyl aluminum hydride in an inert solvent. Low reaction temperatures are preferred and −60° to −70° C. are usual. However, higher temperature may be employed if over-reduction does not occur. 8 is purified, if desired, by column chromatography.

8→9 is a Wittig condensation in which hemiacetal 8 is reacted with (4-carbohydroxy-n-butyl)triphenylphosphonium bromide in dimethyl sulfoxide, in the presence of sodium methylsulfinyl methide. 9 is purified as above.

The conversion 9→12 is an acidic hydrolysis of the tetrahydrophranyl groups. Any acid may be used which does not cause destruction of the molecule in the course of the removal of the protecting group; however, this is accomplished most often by use of 65% aqueous acetic acid. The product is purified as above.

9→10 is an oxidation of the secondary alcohol 9 to the ketone 10. This may be accomplished using any oxidizing agent which does not attack double bonds; however, the Jones reagent is usually preferred. The product is purified as above.

10→11 is carried out in the same manner as 9→12. The product is purified as above.

11→15 is an acid-catalyzed dehydration. Any acid may be used for the process which does not cause extensive decomposition of the product, but the most usual procedure consists of dissolving 11 in an excess of 97% formic acid followed by dilution with ice water and extraction of the product after the starting material has been consumed. The product is purified as above.

As is illustrated in Scheme C, 5 may be substituted for 4 in Scheme B to provide prostaglandin derivatives 12'−15'.

As illustrated in Scheme C, 9 can be used as both a precursor to a 13,14-dihydro 15-substituted-ω-pentanorprostaglandin of the "2-series" as described above or as an intermediate to 16, a precursor to a 13,14-dihydro-15-substituted-ω-pentanorprostaglandin of the "1-series". 9 16 is carried out by catalytic hydrogenation using the catalyst such as rhodium, palladium or platinum or using a homogeneous catalyst such as tris-triphenylphosphine-chlororhodium (I).

In the foregoing procedures, where purification by chromatography is desired, appropriate chromatographic supports include neutral alumina and silica gel and 60–200 mesh silica gel is generally preferred. The chromatography is suitably conducted in reaction-inert solvents such as ether, ethyl acetate, benzene, chloroform, methylene chloride, cyclohexane and n-hexane, as further illustrated in the appended examples.

In numerous in vivo and in vitro tests we have demonstrated that the new prostaglandin analogs possess physiological activities comparable to those exhibited by the natural prostaglandins (see above). These tests include, among others, a test for effect on isolated smooth muscle from guinea pig uterus, guinea pig ileum and rat uterus, inhibition of norepinephrine-induced lipolysis in isolated rat fat cells, inhibition of histamine-induced bronchospasm in the guinea pig effect, on dog blood pressure, inhibition of stress-induced ulceration in the rat, inhibition of pentagastrin-induced hydrochloric acid excretion in rat and dog, inhibition of ADP- or collagen-induced aggregation of blood platelets and effect on diarrhea in mice.

The physiological responses observed in these tests are useful in determining the utility of the test substance for the treatment of various natural and pathological conditions. Such determined utilities include: antihypertensive activity, bronchodilator activity, vasodilator activity, antithrombogenic activity, antiarrhythmic activity, cardiac stimulant activity, and antiulcer activity.

The novel compounds of this invention possess highly selective activity profiles compared with the corresponding naturally occurring prostaglandins and, in many cases, exhibit a longer duration of action. A prime example of the therapeutic importance of these prostaglandin analogs is the efficacy of 15-phenyl-13,14-dihydro-$\omega$-pentanorprostaglandin $E_2$ which is a highly selective bronchodilator without having significant hypotensive activity. Similarly, the other 15 aryl-$\omega$-pentanorprostaglandins of the E or A series display desirable bronchodilator activity.

Similarly, the 15-aryl-13,14-dihydropentanorprostaglandins $F_{2\alpha}$ compounds of this invention exhibits uterine smooth muscle stimulating activity useful for fertility control, abortion, induction of labor and synchronization of oestrus in domestic animals while at the same time having reduced blood pressure effects.

All of the prostaglandins of this invention are also useful in the forms of their salts with pharmaceutically acceptable cations. Furthermore, esters at $C_9$, $C_{11}$ and $C_{15}$ in which the acyl group is lower alkanoyl, formyl, or benzoyl likewise share the utilities of the prostaglandin from which they are derived. In some cases a lower incidence of undesirable side effects accompanies the use of these esters as compared with the corresponding unesterified prostaglandins. It is obvious to one skilled in the art that these compounds include mono esters in the case of a prostaglandin of the A series, diesters in the case of prostaglandins of the E series and triesters in the case of the F series. Such esters are readily prepared by standard methods well known in the art.

The prostaglandin analogs which have a beta hydroxyl at C15 and possess a C15 lower alkyl group have action which is similar to their epimers. In some cases, however, the selectivity that these compounds display exceeds that of the epimeric compounds.

The new compounds of this invention can be used in a variety of pharmaceutical preparations which contain the compound or a pharmaceutically acceptable salt thereof, and they may be administered in the same manner as natural prostaglandins by a variety of routes, such as intravenous, oral and topical, including aerosol, intravaginal, and intranasal, among others.

To produce bronchodilation, an appropriate dosage form would be an aqueous ethanolic solution of a 15 Ar-substituted-$\omega$-pentanorprostaglandin of the A or E series employed as an aerosol using fluorinated hydrocarbons as propellant in the amount of from about 3–500 $\mu$g/dose with up to 16 doses per day.

For induction of abortion tablets or an aqueous suspension of 15-phenyl-13,14-dihydro-$\omega$-pentanorprostaglandin $F_{2\alpha}$ would appropriately be administered at oral doses of about 1–20 mg., with 1–7 doses per day being employed. For intravaginal administration a suitable formulation would be lactose tablets or an impregnated tampon of the same agent. For such treatment suitable doses would be from about 1–20 mg/dose with 1–7 doses being employed.

For synchronization of oestrus in domestic animals an aqueous suspension of 15-phenyl-13,14-dihydro-$\omega$-pentanorprostaglandins $F_{2\alpha}$ would be administered by an IM injection of about 0.5–50 mg with 1–4 doses being employed.

Each of the novel compounds of the present invention are also useful in the form of their $C_1$ esters. Examples of preferred esters are those wherein the esterifying group is alkyl of from one to twelve carbon atoms; cycloalkyl or from three to eight carbon atoms; aralkyl of from seven to nine carbon atoms; phenyl or $\beta$-naphthyl or mono substituted phenyl, or $\beta$-naphthyl wherein said substituent is:

Halo, lower alkyl, lower alkoxyl or phenyl. Especially preferred are the p-biphenyl esters. These specific esters are valuable because they are very easily crystallized, thereby affording the opportunity to recover them in highly pure form and outstanding yield whereas prostaglandins in general ordinarily present severe crystallization problems. The new para-biphenyl esters exhibit the activities of the corresponding parent novel compounds and in addition possess the advantage of a flattened activity versus time curve which is often advantageous. They furthermore have reduced effects on gastrointestinal smooth muscle as evidenced by the reduction of side effects such as diarrhea. The new compounds in the form of the para-phenylphenol esters are prepared by procedures already described with appropriate substitution of corresponding intermediates in para-phenylphenol ester form for the intermediates employed in the foregoing reaction schemes. Thus, for example, compounds 9 and 10 may be esterified with para-phenylphenol in the presence of dicyclohexyl carbodiimide to provide para-phenylphenol esters of precursors to 15 omega pentanorprostaglandin para-phenylphenol esters. These can, through steps 9–12, 10–11 and 11–12, be converted to the novel para-phenylphenol esters mentioned above. Further, compounds 11, 12 and 15 can likewise be esterified with para-phenylphenol and dicyclohexylcarbodiimide to provide the desired esters.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary substances such as preserving agents, wetting agents, stabilizing agent, or other therapeutic agents such as antibiotics.

The following examples are merely illustrative, and in no way limit the scope of the appended claims. In these examples it will be appreciated that all temperatures are expressed in Centigrade, all melting and boiling points are uncorrected and all biological test data is expressed in terms of % activity of $PGE_2$ or administered at the same level (i.e., $PGE_2 = 100$) unless otherwise noted.

The biological data given below was obtained using the following test procedures:

Histamine-Induced Bronchoconstriction—Guinea Pigs

Bronchodilator activities were evaluated in conscious female Reed-Willet guinea pigs (200 to 250 g) fasted overnight according to the method of Van Arman, Miller and O'Malley[1]. At a pre-selected interval (pre-challenge interval) following oral or aerosol administration of water or the test drug in water, each animal was challenged with histamine aerosol as follows: a 0.4% aqueous solution of histamine was placed in a Vaponephrine Standard Nebulizer (Vaponephrine Company, Edison, New Jersey) and sprayed under an air pressure of 6 lb/in$^2$ into a closed $8 \times 8 \times 12$ inch transparent plastic container for one min. Immediately thereafter, the guinea pig was placed in the container. The respiratory status (a reflection of bronchoconstriction) of the guinea pig after one min in the container was scored as follows: 0, normal breathing; 1, slightly deepened breathing; 2, labored breathing; 3, severely labored breathing and ataxia; 4, unconsciousess. The scores for a control group and a test group (8 animals/group) were summed and compared and the difference expressed as percent protection.[1]

[1] VAN ARMAN, C. G., Miller, L. M. and O'Malley, M. P.: SC-10,049: a catacholamine bronchodilator and hyperglycemic agent. J. Pharmacol. Exp. Ther. 133 90–97, 1961.

Dog Blood Pressure

Mongrel dogs were anesthetized with sodium pentobarbitol, 30 mg/kg/i.v. Femoral artery blood pressure was measured with a mercury manometer and recorded on smoked paper and heart rate was determined from electrocardiograms recorded from subcutaneous electrodes. Drugs were given through a cannula in a femoral vein.

Isolated Gastrointestinal and Reproductive Tissue

All measurements were made in a 2 ml tissue bath using a Phipps-Bird Linear Motion Transducer model ST-2. Tissues were allowed to respond to a stable maximum, at which point they were washed and allowed to return to baseline condition. All determinations are an average of at least three individual tissues at each reported dose. Data for analogs were compared to the dose response obtained for a natural PG in a given tissue. For purposes of potency comparisons, a standard dose of natural PG was selected; and all responses were calculated as a percentage of its response. Additional data were recorded as minimum effective dose (MED) and a consistently effective dose (CED) to establish compound detection levels for each tissue. A standard equivalent dose (SED) was determined. This value was defined as the amount of compound (ng/ml) which yielded a response that was equivalent to the tissue's response to a given dose of standard PG.

Guinea Pig Ileum

The ileum was dissected from 200–300 g male guinea pigs sacrificed by cervical dislocation. The tissue was suspended in 2 ml Tyrode solution[2] at 37° C. $PGE_2$ (30 ng/ml) and/or $PGF_{2\alpha}$ (30 ng/ml) were used to establish tissue activity.

[2] Hale, L. J. ed. Biol. Lab Data. p. 92, 1958.

Guinea Pig Uterus[3]

Nulliparous females (300–400 g) which were not in estrus were sacrificed by cervical dislocation. The dissected uteri were incubated in 2 ml of a modified Krebs solution[4] at 37° C. Uterine activity was established using $PGE_2$ (1.0 ng/ml) and/or $PGF_{2\alpha}$ (10 ng/ml).

[3] Clegg, P. C., P. Hopkinson and V. R. Pickles. J. Physiol. 167:1, 1963.
[4] W. S. Umbreit, R. H. Burris and J. F. Stauffer. Monometric Techniques 148, 1957.

EXAMPLE 1

Dimethyl 2-Oxo-2-phenylethylphosphonate (2a)

A solution of 74.5 g (600 mmoles) dimethyl methylphosphonate (Aldrich) in 750 ml dry tetrahydrofuran was cooled to $-78°$ in a dry nitrogen atmosphere. To the stirred phosphonate solution was added 265 ml of 2.34 M n-butyllithium in hexane solution (Alfa Inorganics, Inc.) dropwise over a period of 30 minutes at such a rate that the reaction temperature never rose above $-65°$. After an additional 5 minutes stirring at $-78°$, 41 g (300 mmole) of methyl azoate was added dropwise at a rate that kept the reaction temperature less than $-70°$ (10 minutes). After 1 hour at $-78°$ the reaction mixture was allowed to warm to ambient temperature, neutralized with 35 ml acetic acid and rotary evaporated to a white gel. The gelatinous material was taken up in 75 ml water, the aqueous phase extracted with 300 ml portions of ether (3x), the combined organic extracts were back-washed (50 cc H$_2$O), dried (MgSO$_4$), and concentrated (water aspirator) to a crude residue and distilled, b.p. 130°–5° (0.04 mm) to give 35 g (29%) dimethyl 2-oxo-2-phenylethylphosphonate (2a).

The nmr spectrum (CDCl$_3$) showed a doublet centered at 3.78δ (J=11.5 cps, 6H) for

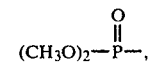

a doublet centered at 3.63δ (J=23 cps, 2H)

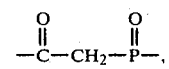

and a multiplet 7.3–8.2δ (5H) for C$_6$H$_5$-.

EXAMPLE 2

2-[3α-n-Phenylbenzoyloxy-5α-hydroxy-2β-(3-oxo-3-phenyl-trans-1-propen-1-yl)-cyclopent-1α-yl]acetic acid, γ-lactone (3a)

Method A

Dimethyl 2-oxo-2-phenylethylphosphonate (2a) (3.4 g, 14.2 mmole) in 225 ml anhydrous ether was treated with 5.9 ml. (9.5 mmole) 1.6 M n-butyllithium in n-hexane (Foote) in a dry nitrogen atmosphere at room temperature. After 5 min. of stirring, an additional 400 ml of anhydrous ether was added, followed by 3.08 g (8.8 mmole) 2-[3α-p-phenylbenzoyloxy-5α-hydroxy-2β-formylcyclopentan-1α-yl]acetic acid, γ-lactone in one portion followed by 75 ml anhydrous ether. After 2 hours, 30 ml anhydrous 1,2-dimethoxyethane was added and the reaction was stirred overnight. The reaction mixture was quenched with 5 ml glacial acetic acid and filtered to yield 2.375 g (69%) 2-[3α-p-phenylbenzoyloxy-5α-hydroxy-2β-(3-oxo-3-phenyl-trans-1-propen-1-yl)cyclopent-1α-yl]acetic acid, γ-lactone (3a) as a solid (m.p. 145°–9°).

The ir spectrum (CHCl₃) of the product (3f) exhibited adsorbtion bands at 1775 cm⁻¹ (strong), 1715 cm⁻¹ (medium) and 1625 cm⁻¹ (medium) attributable to the carbonyl groups and at 975 cm⁻¹ (medium) for the trans double bond.

Method B

Dimethyl 2-oxo-2-phenylpropylphosphonate (2a) (5.17 g, 22.6 mmole) in 30 ml anhydrous 1,2 dimethoxyethane was treated with 9.4 ml. (22 mmole) 2.34 M n-butyllithium in n-hexane (Alfa Inorganics, Inc.) in a dry nitrogen atmosphere at 0°. After 45 min. of stirring at room temperature, 7.6 g (21.4 mmole) 2-[3α-p-phenylbenzoyloxy-5α-hydroxy-2β-formylcyclopentan-1α-yl]acetic acid, γ-lactone was added in one portion followed by 15 ml anhydrous 1,2-dimethoxyethane. After 30 minutes, the reaction mixture was quenched with 2 ml glacial acetic acid, combined with 200 ml CH₂Cl₂ and extracted successively with 75 ml water (2x), 75 ml saturated sodium bicarbonate solution (2x), 75 ml saturated brine (1x), dried (Na₂SO₄) and evaporated to yield 8.2 g (85%) 2-[3α-p-phenylbenzoyloxy-5α-hydroxy-2β-(3-oxo-3-phenyltrans-1-propen-1-yl)cyclopent-1α-yl]acetic acid, γ-lactone (3a) as a solid.

EXAMPLE 3

2-[3a-p-Phenylbenzoyloxy-5α-hydroxy-2β-(3-hydroxy-3-phenyl-1-prop-1-yl)cyclopent-1α-yl]acetic acid, γ-lactone (4a)

To a solution of 7.6 g. (16.8 mmole) 2-[3α-p-phenylbenzoyloxy-5α-hydroxy-2β-(3-oxo-3-phenyl-trans-1-propen-1-yl)cyclopent-1α-yl]acetic acid, γ-lactone (3a) in 100 ml. dry tetrahydrofuran in a dry nitrogen atmosphere at ambient temperature was added dropwise 16.8 ml. of a 0.5 M zinc borohydride solution. After stirring at 25° for 2 hours, a saturated sodium bitartrate solution was added dropwise until hydrogen evolution ceased. The reaction mixture was allowed to stir for 5 minutes, at which time 250 ml. dry methylene chloride was added. After drying (MgSO₄) and concentrating (water aspirator) the resultant semisolid was purified by column chromatography on silica gel (Baker "Analyzed" Reagent 60–200 mesh) using chloroform as eluent. After elution of less polar impurities a fraction containing 2.8 g. of 2-[3α-p-phenylbenzoyloxy-5α-hydroxy-2β-(3-hydroxy-3-phenyl-1-prop-1-yl)cyclopent-1α-yl]acetic acid, γ-lactone (4a) was obtained.

The ir spectrum (CHCl₃) of 4a had strong carbonyl adsorptions at 1770 and 1715 cm⁻¹.

EXAMPLE 4

2-[3α,5α-Dihydroxy-2β-(3α-hydroxy-3-phenyl-prop-1-yl)cyclopent-1α-yl]acetic acid, γ-lactone (6a)

A heterogeneous mixture of 5.3 g (11.6 mmole) of 2-[3α-p-phenylbenzoyloxy-5α-hydroxy-2β-(3-hydroxy-3-phenyl-prop-1-yl)cyclopent-1α-yl]acetic acid, γ-lactone (4a), 60 ml. of absolute methanol and 60 ml of tetrahydrofuran and 1.6 g of finely powdered, anhydrous potassium carbonate was stirred at room temperature for 3 hours, then cooled to 0°. To the cooled solution was added 11.6 ml (11.6 mmole) of 1.0 N aqueous hydrochloric acid. After stirring at 0° for an additional 10 minutes, 60 ml. of water was added with concomitant formation of methyl p-phenylbenzoate which was collected by filtration. The filtrate was saturated with solid sodium chloride, extracted with ethyl acetate (4×10 ml.), the combined organic extracts were washed with saturated sodium bicarbonate (10 ml.) dried (MgSO₄) and concentrated. Purification of the crude residue by silica gel chromatography provided 2.21 g of the desired oily 2-[3α-5α-dihydroxy-2β-(3α-hydroxy-3-phenyl-prop-1-yl)cyclopent-1α-yl]acetic acid, γ-lactone (6a).

EXAMPLE 5

2-[5α-Hydroxy-3α-(tetrahydropyran-2-yloxy)-2β-(3-[tetrahydropyran-2-yloxy]-3-phenyl-prop-1-yl)cyclopent-1α-yl]acetic acid, γ-lactone (7a)

To a solution of 2.21 g (8.0 mmole) 2-[3α,5α-dihydroxy-2β-(3-hydroxy-3-phenyl-prop-1-yl)cyclopent-1α-yl]acetic acid γ-lactone (6a) in 30 ml anhydrous methylene chloride and 3.5 ml of 2,3-dihydropyran at 0° in a dry nitrogen atmosphere was added 20 mg p-toluenesulfonic acid monohydrate. After stirring for 15 minutes, the reaction mixture was combined with 300 ml ether, the ether solution washed with saturated sodium bicarbonate (1×15 ml) then saturated brine (1×15 ml), dried (MgSO₄) and concentrated to yield 3.98 g crude 2-[5α-hydroxy-3α-(tetrahydropyran-2-yloxy)-2β-(3-[tetrahydropyran-2-yloxy]-3-phenyl-prop-1-yl)cyclopent-1α-yl]acetic acid, γ-lactone (7a).

EXAMPLE 6

2-[5α-Hydroxy-3α-(tetrahydropyran-2-yloxy)-2β-(3-[tetrahydropyran-2-yloxy]-3-phenyl-prop-1-yl)cyclopent-1α-yl]acetaldehyde, γ-hemiacetal (8a)

A solution of 3.98 g (8.95 mmole) 2-[5α-hydroxy-3α-(tetrahydropyran-2-yloxy)-2β-(3-[tetrahydropyran-2-yloxy]-3-phenyl-prop-1-yl)cyclopent-1α-yl]acetic acid, γ-lactone (7a) in 30 ml dry toluene was cooled to −78° in a dry nitrogen atmosphere. To this cooled solution was added 13.5 ml of 20% diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature. The reaction mixture was combined with 200 ml ether, washed with 50% sodium potassium tartrate solution (4×50 ml), dried (Na₂SO₄) and concentrated to yield 3.22 g 2-[5α-hydroxy-3α-(tetrahydropyran-2-yloxy)-2β-(3-[tetrahydropyran-2-yloxy]-3-phenyl-prop-1-yl)cyclopent-1α-yl]acetaldehyde, γ-hemiacetal (8a) after purification by silica gel chromatography.

EXAMPLE 7

9α-Hydroxy-11α,15-bis-(tetrahydropyran-2-yloxy)-15-phenyl-cis-5-ω-pentanorprostenoic acid (9a)

To a solution of 10.8 g (25.0 mmole) (4-carbohydroxy-n-butyl) triphenylphosphonium bromide in a dry nitrogen atmosphere in 25 ml dry dimethyl sulfoxide was added 25.0 ml (50.0 mmole) of a 2.0 M solution of sodium methylsufinylmethide in dimethyl sulfoxide. To this red ylide solution was added dropwise a solution of 3225 mg (7.3 mmole) 2-[5α-hydroxy-3α-(tetrahydropyran-2-yloxy)-2β-(3-[tetrahydropyran-2-yloxy]-3-phenyl-prop-1-yl)cyclopent-1α-yl]acetaldehyde, γ-hemiacetal (8a) in 20 ml dry dimethyl sulfoxide over a period of 20 minutes. After an additional 1 hour stirring at room temperature, the reaction mixture was poured into ice water, acidified to pH ~3 with 10% aqueous hydrochloric acid. The acidic solution was extracted with ethyl acetate (3×20 ml) and the combined organic extracts washed once with water (10 ml.), dried (MgSO4) and evaporated to a residue. The residue was purified by column chromatography on silica gel (Baker "Analyzed" Reagent 60–200 mesh) using chloroform then ethyl acetate as eluent. After removal of high $R_f$ impurities, 880 mg of 9α-hydroxy-11α,15-bis-(tetrahydropyran-2-yloxy)-15-phenyl-cis-5-ω-pentanorprostenoic acid (9a) was collected.

EXAMPLE 8

9-Oxo-11α,15-bis-(tetrahydropyran-2-yloxy)-15-phenyl-cis-5-ω-pentanorprostenoic acid (10a)

To a solution cooled to −10° under nitrogen of 1233 mg (2.3 mmole) 9α-hydroxy-11α,15-bis-(tetrahydropyran-2-yloxy)-15-phenyl-cis-5-ω-pentanorprostadienoic acid (9a) in 26 ml. reagent grade acetone was added dropwise to 0.96 ml. (2.65 mmole) of Jones' reagent. After 5 minutes at −10°, 1.5 ml. 2-propanol was added and the reaction mixture was allowed to stir an additional 5 minutes at which time it was combined with 300 ml. ethyl acetate, washed with water (3×50 ml.), dried (MgSO4) and concentrated to give 950 mg. of 9-oxo-11α,15-bis-(tetrahydropyran-2-yloxy)-15-phenyl-cis-5-ω-pentanorprostenoic acid (10a).

EXAMPLE 9

9-Oxo-11α,15-dihydroxy-15-phenyl-cis-5-ω-pentanorprostenoic acid (11a)

A solution of 950 mg. (1.81 mmole) 9-oxo-11α,15-bis-tetrahydropyran-2-yloxy)-15-phenyl-cis-5-ω-pentanorprostenoic acid (10a) in 9.5 ml. of a 65:35 mixture of glacial acetic acid:water was stirred under nitrogen at room temperature for 18 hours and then was concentrated by rotary evaporation. The resultant crude oil was purified by column chromatography on silica gel (Mallinckrodt CC-7 100–200 mesh) using ethyl acetate methylene chloride as eluent. After elution of less polar impurities, the oily 9-oxo-11α,15-dihydroxy-15-phenyl-cis-5-ω-pentanorprostenoic acid (11a) weighing 365 mg. was collected.

EXAMPLE 10

9α,11α,15-Trihydroxy-15-phenyl-cis-5-ω-pentanorprostenoic acid (12a)

A mixture of 600 mg of 9α-hydroxy-11α,15-bis-(tetrahydropyran-2-yloxy)-15-phenyl-cis-5-ω-pentanorprostenoic acid (9a) in 6 ml of a 65:35 mixture of acetic acid:water was stirred under nitrogen at room temperature overnight, then was concentrated under reduced pressure to a viscous oil. The crude product was purified by column chromatography on Mallinckrodt CC-7 silica gel using chloroform:ethyl acetate as eluents. After elution of less polar impurities, the desired 9α,11α,15-trihydroxy-15-phenyl-cis-5-ω-pentanorprostenoic acid (12a) was obtained as a viscous, colorless oil weighing 180 mg.

EXAMPLE 11

9-oxo-15-hydroxy-15-phenyl-cis-5-Δ$^{10,11}$-ω-pentanorprostadienoic acid (15a)

A solution of 50 mg of 9-oxo-11α,15-dihydroxy-15-phenyl-cis-5-ω-pentanorprostadienoic acid (11a) in 10 ml dry methylene chloride and 10 ml formic acid is stirred at room temperature for 5 hours. The reaction mixture is diluted with 50 ml toluene and evaporated to yield (after chromatography) 9-oxo-15-hydroxy-15-phenyl-cis-5-Δ-$^{10,11}$-trans-ω-pentanorprostadienoic acid (15a).

In the same way 15-aryl- -pentanorprostaglandins of the $A_0$ and 13,14 dihydro $A_2$ series may be prepared from 15-aryl-ω-pentanorprostaglandins of the $E_0$ and 13,14 dihydro series respectively.

EXAMPLE 12

9-Oxo-11α,15-dihydroxy-15-phenyl-ω-pentanorprostanoic acid

A heterogeneous solution of 34 mg (0.89 mmole) 9-oxo-11α,15-dihydroxy-15-phenyl-cis-5-ω-pentanorprostenoic acid (11a) and 13 mg of 5% palladium on carbon in 3 ml absolute methanol is hydrogenated (1 atm) at 0° for 2 hours. The reaction mixture is filtered and evaporated to yield 9-oxo-11α,15-dihydroxy-15-phenyl-ω-pentanorprostanoic acid.

In the same way 15-aryl-ω-pentanorprostaglandins of the $F_{2α}$ series may be prepared from 15-aryl-ω-pentanorprostaglandins of the 13,14-dihydro $E_2$ series.

What is claimed is:

1. A compound of the structure:

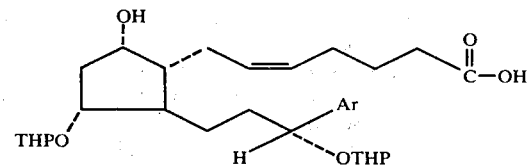

wherein

Ar is α- or β-naphthyl; phenyl; 3,4-dimethoxyphenyl; 3,4-methylenedioxyphenyl; 3,4,5-trimethoxyphenyl; or monosubstituted phenyl wherein said substituent is halo, trifluoromethyl, phenyl, lower alkyl or lower alkoxy and THP is 2-tetrahydropyranyl.

2. A compound of the structure:

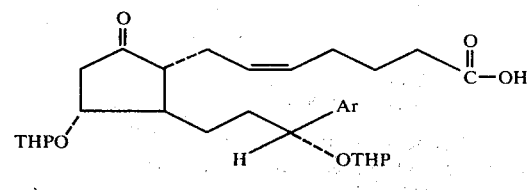

wherein

Ar is α- or β-naphthyl; phenyl; 3,4-dimethoxyphenyl; 3,4-methylenedioxyphenyl; 3,4,5-trimethoxyphenyl; or monosubstituted phenyl wherein said substituent is halo, trifluoromethyl, phenyl, lower alkyl or lower alkoxy and THP is 2-tetrahydropyranyl.

3. The compound of claim 1 wherein Ar is phenyl.

4. The compound of claim 2 wherein Ar is phenyl.

* * * * *